(12) United States Patent
Harding et al.

(10) Patent No.: US 11,123,523 B2
(45) Date of Patent: Sep. 21, 2021

(54) INTRAVENOUS CATHETER DEVICE WITH INTEGRATED EXTENSION TUBE

(71) Applicant: Becton, Dickinson and Company, Franklin Lakes, NJ (US)

(72) Inventors: Weston F. Harding, Lehi, UT (US); Jonathan Karl Burkholz, Salt Lake City, UT (US); Jithendra Kumar, Singapore (SG); Bin Wang, Sandy, UT (US); Bart D. Peterson, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 285 days.

(21) Appl. No.: 16/272,686

(22) Filed: Feb. 11, 2019

(65) Prior Publication Data
US 2019/0167951 A1 Jun. 6, 2019

Related U.S. Application Data

(62) Division of application No. 15/286,281, filed on Oct. 5, 2016, now Pat. No. 10,245,416.
(Continued)

(51) Int. Cl.
*A61M 25/06* (2006.01)
*A61M 39/04* (2006.01)
*A61M 39/22* (2006.01)

(52) U.S. Cl.
CPC ...... *A61M 25/0606* (2013.01); *A61M 25/065* (2013.01); *A61M 25/0693* (2013.01);
(Continued)

(58) Field of Classification Search
CPC .......... A61M 25/0606; A61M 25/0693; A61M 25/01; A61M 25/0097; A61M 39/04; A61M 25/0637; A61M 25/0618; A61M 39/22; A61M 5/1626; A61M 25/06; A61M 25/0612; A61M 25/0631; A61B 5/150473;
(Continued)

(56) References Cited

U.S. PATENT DOCUMENTS 3,046,984 A 7/1962 Eby
3,547,119 A 12/1970 Hall
(Continued)

FOREIGN PATENT DOCUMENTS

CA 2914701 12/2004
CN 1184677 6/1998
(Continued)

OTHER PUBLICATIONS

Silva, Elson, Email Regarding "Respecting Hydrology Science and IP Rights—US Pat. Application 20110130728," pp. 1-6 (Jun. 2, 2011).

*Primary Examiner* — Nilay J Shah
(74) *Attorney, Agent, or Firm* — Kirton McConkie; Craig Metcalf; Kevin Stinger

(57) ABSTRACT

The present invention relates to peripheral intravenous catheters, and in particular to an integrated peripheral intravenous catheter having a low profile securement platform, a needle hub having an interior compartment and further comprising a paddle grip, and an extension tube coupled to the catheter and stored within the interior compartment of the needle hub prior to catheterization.

14 Claims, 9 Drawing Sheets

Related U.S. Application Data

(60) Provisional application No. 62/296,383, filed on Feb. 17, 2016, provisional application No. 62/296,385, filed on Feb. 17, 2016, provisional application No. 62/247,607, filed on Oct. 28, 2015, provisional application No. 62/247,617, filed on Oct. 28, 2015, provisional application No. 62/247,624, filed on Oct. 28, 2015, provisional application No. 62/247,626, filed on Oct. 28, 2015, provisional application No. 62/247,599, filed on Oct. 28, 2015, provisional application No. 62/247,596, filed on Oct. 28, 2015, provisional application No. 62/247,621, filed on Oct. 28, 2015.

(52) U.S. Cl.
CPC ............ *A61M 39/04* (2013.01); *A61M 39/22* (2013.01); *A61M 25/0618* (2013.01); *A61M 25/0637* (2013.01)

(58) Field of Classification Search
CPC ........ A61B 5/150503; A61B 5/150534; A61B 5/150633; A61B 5/150648; A61B 5/150656; A61B 5/15074
See application file for complete search history.

(56) References Cited

U.S. PATENT DOCUMENTS

| | | | |
|---|---|---|---|
| 3,589,361 A | | 6/1971 | Loper |
| 3,827,434 A | * | 8/1974 | Thompson .......... A61M 25/065 604/160 |
| 3,853,127 A | | 12/1974 | Spademan |
| 3,859,998 A | | 1/1975 | Thomas |
| 4,003,403 A | | 1/1977 | Nehring |
| 4,043,346 A | | 8/1977 | Mobley |
| 4,099,528 A | * | 7/1978 | Sorenson ............ A61M 5/1582 604/164.01 |
| 4,149,539 A | | 4/1979 | Cianci |
| 4,172,448 A | | 10/1979 | Brush |
| 4,177,809 A | * | 12/1979 | Moorehead ....... A61M 25/0606 604/165.03 |
| 4,193,399 A | | 3/1980 | Robinson |
| 4,200,096 A | | 4/1980 | Charvin |
| 4,269,186 A | | 5/1981 | Loveless |
| 4,311,137 A | | 1/1982 | Gerard |
| 4,317,445 A | | 3/1982 | Robinson |
| 4,326,519 A | * | 4/1982 | D'Alo ............... A61M 25/0637 604/165.04 |
| 4,353,369 A | | 10/1982 | Muetterties |
| 4,362,156 A | | 12/1982 | Feller, Jr. |
| 4,365,630 A | | 12/1982 | McFarlane |
| 4,387,879 A | | 6/1983 | Tauschinski |
| 4,419,094 A | | 12/1983 | Patel |
| 4,445,893 A | | 5/1984 | Bodicky |
| 4,449,693 A | | 5/1984 | Gereg |
| 4,496,348 A | | 1/1985 | Genese |
| 4,525,157 A | | 6/1985 | Vaillancourt |
| 4,531,935 A | | 7/1985 | Berryessa |
| 4,682,980 A | | 7/1987 | Suzuki |
| 4,701,162 A | * | 10/1987 | Rosenberg ........ A61M 25/0009 604/103 |
| 4,703,761 A | | 11/1987 | Rathbone |
| 4,758,225 A | | 7/1988 | Cox et al. |
| 4,765,588 A | | 8/1988 | Atkinson |
| 4,772,264 A | | 9/1988 | Cragg |
| 4,813,939 A | | 3/1989 | Marcus |
| 4,834,708 A | | 5/1989 | Pillari |
| 4,842,591 A | | 6/1989 | Luther |
| 4,874,377 A | | 10/1989 | Newgard et al. |
| 4,894,052 A | | 1/1990 | Crawford |
| 4,917,668 A | | 4/1990 | Haindl |
| 4,917,671 A | | 4/1990 | Chang |
| 4,925,444 A | * | 5/1990 | Orkin ................ A61M 5/16827 123/DIG. 13 |
| 4,935,010 A | | 6/1990 | Cox |
| 4,950,257 A | | 8/1990 | Hibbs et al. |
| 4,966,586 A | | 10/1990 | Vaillancourt |
| D315,822 S | | 3/1991 | Ryan |
| 5,032,116 A | | 7/1991 | Peterson |
| 5,041,097 A | | 8/1991 | Johnson |
| 5,053,014 A | | 10/1991 | Van Heugten |
| 5,057,087 A | | 10/1991 | Harmon |
| 5,059,186 A | | 10/1991 | Yamamoto |
| 5,062,836 A | | 11/1991 | Wendell |
| 5,064,416 A | | 11/1991 | Newgard |
| 5,084,023 A | | 1/1992 | Lemieux |
| 5,085,645 A | | 2/1992 | Purdy et al. |
| 5,108,374 A | | 4/1992 | Lemieux |
| 5,127,905 A | | 7/1992 | Lemieux |
| 5,135,504 A | | 8/1992 | McLees |
| 5,154,703 A | | 10/1992 | Bonaldo |
| 5,156,596 A | | 10/1992 | Balbierz |
| 5,176,653 A | | 1/1993 | Metals |
| 5,176,662 A | | 1/1993 | Bartholomew |
| 5,186,712 A | | 2/1993 | Kelso |
| 5,201,717 A | | 4/1993 | Wyatt |
| 5,211,634 A | | 5/1993 | Vaillancourt |
| 5,215,525 A | | 6/1993 | Sturman |
| 5,215,528 A | | 6/1993 | Purdy |
| 5,215,529 A | | 6/1993 | Fields |
| 5,226,883 A | | 7/1993 | Katsaros |
| 5,234,410 A | | 8/1993 | Graham |
| 5,242,411 A | | 9/1993 | Yamamoto |
| 5,254,097 A | | 10/1993 | Schock |
| 5,267,971 A | | 12/1993 | Brimhall |
| 5,269,764 A | | 12/1993 | Vetter et al. |
| 5,273,546 A | | 12/1993 | McLaughlin |
| 5,290,222 A | | 3/1994 | Feng |
| 5,290,246 A | | 3/1994 | Yamamoto |
| 5,295,969 A | | 3/1994 | Fischell |
| 5,300,045 A | * | 4/1994 | Plassche, Jr. ....... A61M 5/3273 604/158 |
| 5,306,243 A | | 4/1994 | Bonaldo |
| 5,312,359 A | * | 5/1994 | Wallace ............ A61M 25/0631 604/164.08 |
| 5,328,482 A | | 7/1994 | Sircom |
| 5,330,435 A | | 7/1994 | Vaillancourt |
| 5,342,315 A | | 8/1994 | Rowe |
| 5,350,363 A | | 9/1994 | Goode |
| 5,352,205 A | | 10/1994 | Dales |
| 5,354,281 A | | 10/1994 | Chen |
| 5,356,381 A | | 10/1994 | Ensminger |
| 5,368,029 A | | 11/1994 | Holcombe |
| 5,405,323 A | | 4/1995 | Rogers |
| 5,447,501 A | | 9/1995 | Karlsson |
| 5,456,675 A | | 10/1995 | Wolbring |
| 5,458,658 A | | 10/1995 | Sircom |
| 5,487,728 A | | 1/1996 | Vaillancourt |
| 5,498,241 A | | 3/1996 | Fabozzi |
| 5,509,912 A | | 4/1996 | Vaillancourt |
| 5,520,666 A | | 5/1996 | Choudhury |
| 5,542,932 A | | 8/1996 | Daugherty |
| 5,549,566 A | | 8/1996 | Elias |
| 5,549,576 A | | 8/1996 | Patterson |
| 5,549,577 A | | 8/1996 | Siegel |
| 5,562,631 A | | 10/1996 | Bogert |
| 5,562,633 A | | 10/1996 | Wozencroft |
| 5,573,510 A | | 11/1996 | Isaacson |
| 5,575,769 A | | 11/1996 | Vaillancourt |
| 5,575,777 A | | 11/1996 | Cover |
| 5,584,809 A | | 12/1996 | Gaba |
| 5,599,310 A | | 2/1997 | Bogert |
| 5,601,536 A | | 2/1997 | Crawford |
| 5,613,663 A | | 3/1997 | Schmidt |
| 5,651,772 A | | 7/1997 | Arnett |
| 5,657,963 A | | 8/1997 | Hinchliffe |
| 5,676,656 A | | 10/1997 | Brimhall |
| 5,690,612 A | | 11/1997 | Lopez et al. |
| 5,690,619 A | | 11/1997 | Erskine |
| 5,697,907 A | | 12/1997 | Gaba |

(56) References Cited

U.S. PATENT DOCUMENTS

| | | | |
|---|---|---|---|
| 5,697,914 A * | 12/1997 | Brimhall | A61M 25/0637 604/164.01 |
| 5,697,915 A | 12/1997 | Lynn | |
| 5,699,821 A | 12/1997 | Paradis | |
| 5,700,244 A | 12/1997 | Kriesel | |
| 5,700,250 A | 12/1997 | Erskine | |
| 5,704,919 A | 1/1998 | Kraus | |
| 5,718,688 A | 2/1998 | Wozencroft | |
| 5,730,123 A | 3/1998 | Lorenzen | |
| 5,738,144 A | 4/1998 | Rogers | |
| 5,749,856 A | 5/1998 | Zadini | |
| 5,749,861 A | 5/1998 | Guala | |
| 5,772,636 A * | 6/1998 | Brimhall | A61M 25/0631 604/164.01 |
| 5,800,399 A | 9/1998 | Bogert et al. | |
| 5,806,831 A | 9/1998 | Paradis | |
| 5,810,780 A | 9/1998 | Brimhall | |
| 5,810,835 A * | 9/1998 | Ryan | A61M 25/0084 604/159 |
| 5,817,069 A | 10/1998 | Arnett | |
| 5,843,046 A | 12/1998 | Motisi et al. | |
| 5,853,393 A | 12/1998 | Bogert | |
| 5,882,345 A | 3/1999 | Yoon | |
| 5,911,710 A | 6/1999 | Barry et al. | |
| 5,935,109 A | 8/1999 | Donnan | |
| 5,935,110 A | 8/1999 | Brimhall | |
| 5,947,932 A | 9/1999 | Desecki | |
| 5,954,698 A | 9/1999 | Pike | |
| 5,961,497 A | 10/1999 | Larkin | |
| 5,967,490 A | 10/1999 | Pike | |
| 6,039,302 A | 3/2000 | Cote, Sr. et al. | |
| 6,056,726 A | 5/2000 | Isaacson | |
| 6,077,244 A | 6/2000 | Botich | |
| 6,117,108 A | 9/2000 | Woehr et al. | |
| 6,142,981 A | 11/2000 | Heck | |
| 6,156,010 A | 12/2000 | Kuracina et al. | |
| 6,171,287 B1 | 1/2001 | Lynn et al. | |
| 6,206,851 B1 | 3/2001 | Prosl | |
| 6,221,047 B1 | 4/2001 | Greene | |
| 6,224,569 B1 | 5/2001 | Brimhall | |
| 6,273,869 B1 | 8/2001 | Vaillancourt | |
| 6,287,278 B1 | 9/2001 | Woehr | |
| D451,599 S | 12/2001 | Crawford et al. | |
| D451,600 S | 12/2001 | Crawford et al. | |
| 6,379,332 B1 | 4/2002 | Van Landuyt | |
| D458,678 S | 6/2002 | Cindrich | |
| 6,440,119 B1 | 8/2002 | Nakada et al. | |
| 6,461,362 B1 | 10/2002 | Halseth | |
| 6,485,473 B1 | 11/2002 | Lynn | |
| 6,497,994 B1 | 12/2002 | Kafrawy | |
| 6,506,181 B2 | 1/2003 | Meng | |
| D469,870 S | 2/2003 | Niermann et al. | |
| 6,565,542 B2 | 5/2003 | Kumar | |
| 6,575,960 B2 | 6/2003 | Becker et al. | |
| 6,595,954 B1 | 7/2003 | Luther | |
| 6,595,981 B2 | 7/2003 | Huet | |
| 6,616,630 B1 | 9/2003 | Woehr | |
| 6,652,486 B2 | 11/2003 | Bialecki | |
| 6,663,592 B2 | 12/2003 | Rhad | |
| 6,689,102 B2 | 2/2004 | Greene | |
| 6,695,814 B2 | 2/2004 | Greene | |
| 6,709,419 B2 | 3/2004 | Woehr | |
| 6,740,063 B2 * | 5/2004 | Lynn | A61M 25/0606 604/256 |
| D491,266 S | 6/2004 | Cindrich et al. | |
| D492,031 S | 6/2004 | Cindrich et al. | |
| 6,749,588 B1 | 6/2004 | Howell | |
| D492,774 S | 7/2004 | Cindrich et al. | |
| 6,837,884 B2 | 1/2005 | Woloszko | |
| D592,302 S | 5/2009 | Stokes et al. | |
| 7,670,317 B2 | 3/2010 | Cindrich et al. | |
| 7,694,403 B2 | 4/2010 | Moulton | |
| 7,736,339 B2 | 6/2010 | Woehr et al. | |
| 7,905,856 B2 | 3/2011 | McGuckin, Jr. et al. | |
| 7,914,494 B2 | 3/2011 | Hiejima | |
| 8,066,670 B2 | 11/2011 | Cluff | |
| 8,066,675 B2 | 11/2011 | Cindrich | |
| 8,070,725 B2 | 12/2011 | Christensen | |
| 8,357,119 B2 | 1/2013 | Stout et al. | |
| 8,361,020 B2 | 1/2013 | Stout et al. | |
| 8,388,583 B2 | 3/2013 | Stout et al. | |
| 8,574,203 B2 | 11/2013 | Stout et al. | |
| 8,591,473 B2 | 11/2013 | Jones et al. | |
| 8,679,063 B2 | 3/2014 | Stout et al. | |
| 8,702,658 B2 | 4/2014 | Spearman | |
| D713,522 S | 9/2014 | Woehr et al. | |
| D819,802 S | 6/2018 | Burkholz et al. | |
| D835,262 S | 12/2018 | Burkholz et al. | |
| D837,368 S | 1/2019 | Burkholz et al. | |
| 10,245,416 B2 | 4/2019 | Harding et al. | |
| 10,814,106 B2 | 10/2020 | Garrison et al. | |
| 2002/0082546 A1 | 6/2002 | Crank et al. | |
| 2002/0177814 A1 | 11/2002 | Meng | |
| 2005/0015071 A1 * | 1/2005 | Brimhall | A61M 25/0693 604/506 |
| 2005/0251092 A1 * | 11/2005 | Howell | A61M 25/0625 604/110 |
| 2005/0277879 A1 | 12/2005 | Daga | |
| 2006/0264833 A1 | 11/2006 | Moulton | |
| 2007/0010796 A1 | 1/2007 | Moran et al. | |
| 2007/0093778 A1 | 4/2007 | Cindrich et al. | |
| 2007/0225648 A1 | 9/2007 | Winsor et al. | |
| 2007/0270758 A1 | 11/2007 | Hanner | |
| 2008/0103449 A1 * | 5/2008 | Murashita | A61M 25/0637 604/164.08 |
| 2008/0167577 A1 | 7/2008 | Weilbacher et al. | |
| 2009/0054845 A1 | 2/2009 | Puhasmagi | |
| 2009/0287189 A1 | 11/2009 | Suwito | |
| 2010/0280455 A1 | 11/2010 | Ogawa et al. | |
| 2011/0054403 A1 | 3/2011 | Tanabe et al. | |
| 2013/0150793 A1 | 6/2013 | Beissel et al. | |
| 2013/0218082 A1 | 8/2013 | Hyer et al. | |
| 2013/0237925 A1 | 9/2013 | Trainer et al. | |
| 2014/0107584 A1 * | 4/2014 | Rosenberg | A61M 25/02 604/178 |
| 2014/0364809 A1 | 12/2014 | Isaacson et al. | |
| 2015/0224296 A1 | 8/2015 | Winsor | |
| 2017/0120008 A1 | 5/2017 | Burkholz et al. | |
| 2017/0120014 A1 | 5/2017 | Harding et al. | |
| 2017/0216535 A1 | 8/2017 | Mao | |
| 2017/0347913 A1 | 12/2017 | Isaacson et al. | |

FOREIGN PATENT DOCUMENTS

| | | |
|---|---|---|
| CN | 101296720 | 10/2008 |
| CN | 101321549 | 12/2008 |
| CN | 202909200 | 5/2013 |
| CN | 203852671 | 10/2014 |
| CN | 102710541 B | 3/2016 |
| CN | 207168789 | 4/2018 |
| EP | 0268480 B1 | 10/1990 |
| EP | 1016429 | 7/2000 |
| EP | 0732120 B1 | 5/2003 |
| EP | 1306097 B1 | 5/2003 |
| EP | 0993839 B1 | 9/2004 |
| EP | 1679043 B1 | 12/2007 |
| EP | 2022421 A1 | 2/2009 |
| GB | 2508466 B | 10/2014 |
| JP | S56102253 | 8/1981 |
| JP | S5832774 | 2/1983 |
| JP | S61-253073 | 11/1986 |
| JP | H06-086814 | 3/1994 |
| JP | H06-086821 | 3/1994 |
| JP | H08257129 | 10/1996 |
| JP | H09-509075 | 9/1997 |
| JP | 2000279527 | 10/2000 |
| JP | 2004528127 | 9/2004 |
| JP | 2005-526526 | 9/2005 |
| JP | 2011045544 A | 3/2011 |
| JP | 2012521796 | 9/2012 |
| JP | 2012521797 | 9/2012 |
| JP | 2012200425 | 10/2012 |
| JP | 3188771 | 1/2014 |

(56) References Cited

FOREIGN PATENT DOCUMENTS

| | | |
|---|---|---|
| JP | 2014108112 | 6/2014 |
| WO | WO-8807388 A1 | 10/1988 |
| WO | WO-9745151 A1 | 12/1997 |
| WO | 9842393 | 10/1998 |
| WO | 02/096494 | 12/2001 |
| WO | 02096495 | 12/2002 |
| WO | WO-02096495 A2 | 12/2002 |
| WO | WO-2004/082727 | 9/2004 |
| WO | 2004/087247 | 10/2004 |
| WO | WO-2004098685 A1 | 11/2004 |
| WO | WO-2006037638 A1 | 4/2006 |
| WO | 2007/052655 | 5/2007 |
| WO | WO-2010111283 A1 | 9/2010 |
| WO | WO-2011/055287 | 5/2011 |
| WO | 2015/161299 | 10/2015 |
| WO | WO-2016/007442 | 1/2016 |
| WO | 2017062579 | 4/2017 |
| WO | WO-2017062579 A1 | 4/2017 |

* cited by examiner

INTRAVENOUS CATHETER DEVICE WITH INTEGRATED EXTENSION TUBE

RELATED APPLICATIONS

This application is a divisional of U.S. patent application Ser. No. 15/286,281, filed Oct. 5, 2016, and entitled INTRAVENOUS CATHETER DEVICE WITH INTEGRATED EXTENSION TUBE, which claims the benefit of U.S. Provisional Patent Application No. 62/247,599, which was filed Oct. 28, 2015, U.S. Provisional Patent Application No. 62/247,596, which was filed on Oct. 28, 2015, U.S. Provisional Patent Application No. 62/296,383, which was filed on Feb. 17, 2016, U.S. Provisional Patent Application No. 62/247,617, which was filed on Oct. 28, 2015, U.S. Provisional Patent Application Ser. No. 62/247,607, which was filed Oct. 28, 2015, U.S. Provisional Patent Application Ser. No. 62/247,621, which was filed Oct. 28, 2015, U.S. Provisional Patent Application Ser. No. 62/247,624, which was filed Oct. 28, 2015, U.S. Provisional Application No. 62/247,626, which was filed on Oct. 28, 2015, and U.S. Provisional Application No. 62/296,385, which was filed on Feb. 17, 2016, each of which is incorporated herein by reference in their entirety.

BACKGROUND OF THE INVENTION

In medicine, an intravenous is a catheter placed into a peripheral vein in order to administer medications or fluids to a patient in need. An intravenous catheter may also be used to draw blood.

The catheter is introduced into the patient's vein by an introducer needle that is positioned within the lumen of the catheter, such that a sharpened tip of the needle is exposed beyond the distal tip of the catheter. The sharpened tip punctures the skin and vein of the patient to provide a pathway through which the distal tip of the catheter may be advanced. Once the catheter tip is placed into the vein, the needle tip is withdrawn into the catheter; a technique commonly referred to as "hooding". The catheter and needle are then advanced into the vein to a desired depth, after which the needle is entirely removed from the catheter. The catheter is then secured to the patient's skin by an adhesive strip or wrapping.

Generally a catheter is coupled to a catheter adapter having a blood control device, such as a valve or septum. As such, blood flowing through the catheter is retained within the catheter adapter until the blood control device is actuated or otherwise manipulated to permit flow through the catheter and catheter adapter.

An extension tube generally comprises a flexible section of tubing having a first end that is configured to compatibly couple to a catheter or catheter adapter, and further comprises a second end that may be accessed directly by a syringe or needle, or may be further coupled to an intravenous bag by a section of intravenous tubing. As a common practice, an extension tube is coupled to the catheter adapter following placement of the catheter. In some instances, a clinician may be required to manually occlude the patient's vein and/or the catheter while simultaneously attaching an extension tube thereto. In other instances, a clinician must take care to immobilize the catheter and/or catheter adapter while attaching the extension tube to prevent accidental removal of the inserted catheter. Further, in many instances a clinician is required to sterilize the mating ends of the catheter adapter and the extension tube prior to making the connection, thus adding an additional step to the procedure.

Thus, although methods and devices currently exist for accessing the vasculature of a patient via a catheter and an extension tube, challenges still remain. Accordingly, the features of the present invention address and overcome these challenges.

BRIEF SUMMARY OF THE INVENTION

The present invention relates to peripheral intravenous catheters, and in particular to an integrated peripheral intravenous catheter having a low profile securement platform, a needle hub having an interior compartment and further comprising a paddle grip, and an extension tube coupled to the catheter and stored within the interior compartment of the needle hub prior to insertion of the catheter.

Some implementations of the present invention comprise an intravenous catheter device having a catheter adapter having a proximal end, a distal end, and a lumen interposed therebetween. The catheter adapter further comprises a securement platform that is constructed of a soft, pliable or flexible material, such as a soft polymer. In some instances, the securement platform comprises a soft, polymer material comprising a Shore A durometer hardness of from approximately 15 to 100. In some instances, the soft, polymer material comprises a durometer hardness of from approximately 30 Shore A to approximately 90 Shore D. In some instances, the soft, polymer material comprises a durometer hardness of from approximately 50 Shore A to approximately 90 Shore D. In some instances, the distal end of the catheter adapter comprises an intravenous catheter in fluid communication with the lumen. Further, the proximal end of the catheter adapter comprises an extension tube that is also in fluid communication with the lumen. In some instances, securement platform may further comprise a hard or rigid plastic polymer material.

Some implementations of the present invention further comprise a needle hub comprising a rigid material, such as a hard plastic material. The needle hub comprises an open end, a closed end, and a compartment interposed therebetween. The closed end is configured to receive a terminal end of the extension tube, and the open end is configured to receive the proximal end of the catheter adapter, wherein the extension tube is stored within the compartment. In some instances, the extension tube is wound around an outer surface of the needle hub. In some instances, the closed end further comprises a flashback chamber in fluid communication with an interior lumen of the introducer needle.

In some instances, the needle hub further comprises a paddle grip positioned in proximity to the open end and arranged to overlap the securement platform, thereby permitting the user to pinch the paddle grip and securement platform between their thumb and index finger during the process of catheterization. In some instances, the overlapping arrangement of the paddle grip and the securement platform permits the user to hood the tip end of the needle by adjusting their grip to move the securement platform and paddle grip in opposite directions.

The needle hub further comprises an introducer needle having a base end, a tip end, and a body extending therebetween. The base end of the needle is securely attached to the closed end of the needle hub. When assembled, the body of the needle extends outwardly from the closed end, through the proximal end, the lumen, the distal end, and the intravenous catheter, such that the tip end of the needle is exposed beyond a terminal end of the intravenous catheter.

Some implementations of the present invention are further configured such that the body of the introducer needle passes through an interior of the extension tube when the intravenous catheter device is assembled. In some instances, the extension tube is wound around the body of the introducer needle within the compartment.

In some instances, the proximal end of the catheter adapter, and/or the terminal end of the extension tube further comprises a blood control device, such as a valve, a self-sealing polymer, a luer adapter, or a septum. In some instances, the blood control valve comprises a passageway through which the body of the introducer needle passes. In some instances, the blood control device is a single-use device. In other instances, the blood control device is a multi-use device.

Some implementations of the present invention further comprise an extension tube having an access port that is coupled to a sidewall surface of the extension tube, and extending outwardly therefrom. For these embodiments, the needle hub further comprises an access slot extending proximally from the open end to a position that is in proximity to the closed end, whereby the access port passes through the access slot and is located externally to the compartment of the needle hub with the intravenous catheter device is assembled. In some instances, the open end of the needle hub further comprises a notch having a width and depth that is configured to receive and support a proximal edge of the securement platform of the catheter adapter.

Some implementations of the present invention further comprise one or more features designed to capture and shield the tip end of the introducer needle following catheterization of the patient. For example, in some instances the proximal end of the extension tube further comprises a needle shield or safety mechanism that is selectively coupled thereto and through which the body of the introducer needle passes when the device is assembled. Upon removal of the introducer needle from the extension tube, a needle feature, such as a ferrule or notch, actuates the safety mechanism to selectively disengage the safety mechanism from the terminal end of the extension tube. Once released, the safety mechanism captures the tip end of the needle, thereby preventing unintended exposure to the tip end of the needle.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1A:
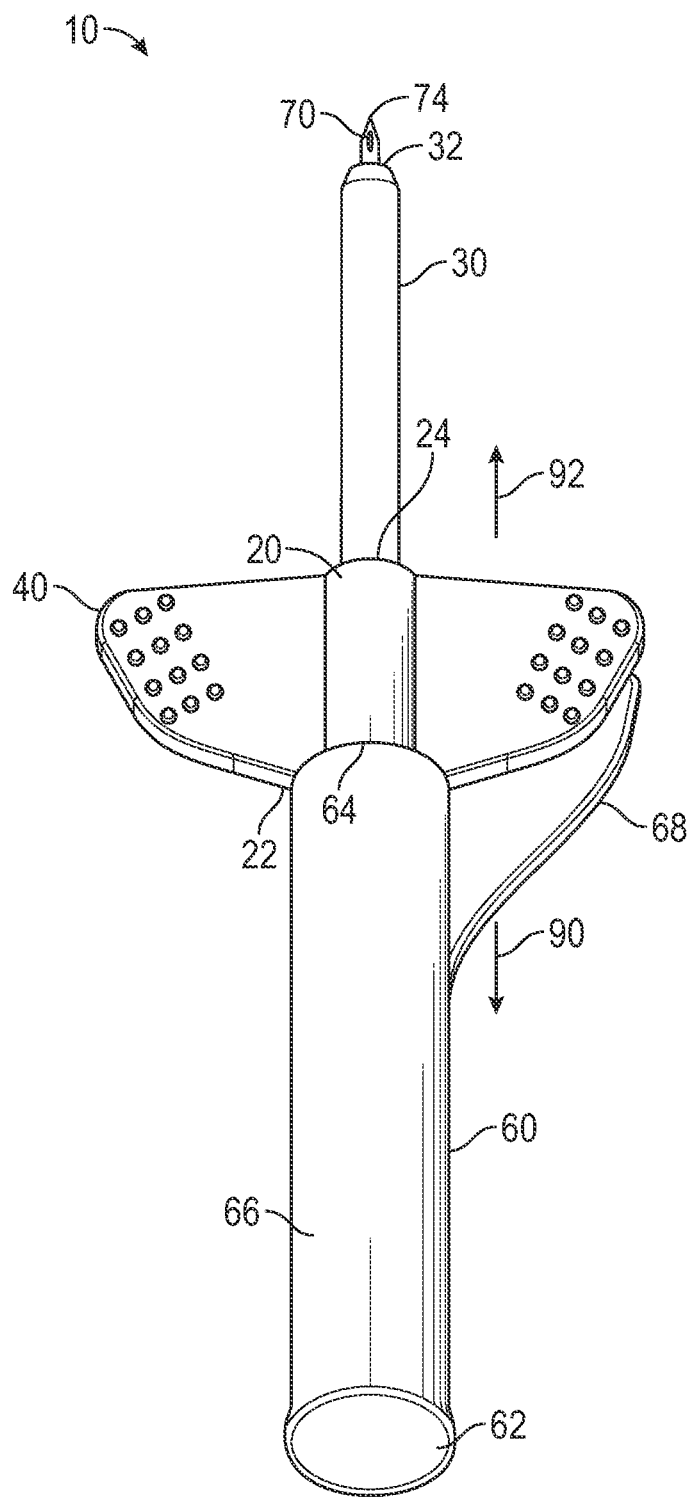
FIG. 1A is a perspective top view of an assembled intravenous catheter device in accordance with a representative embodiment of the present invention.

The present invention relates to peripheral intravenous catheters, and in particular to an integrated peripheral intravenous catheter having a low profile securement platform, a needle hub having an interior compartment and further comprising a paddle grip, and an extension tube coupled to the catheter and stored within the interior compartment of the needle hub prior to insertion of the catheter.

Some implementations of the present invention comprise an intravenous catheter device having a catheter adapter having a proximal end, a distal end, and a lumen interposed therebetween. The catheter adapter further comprises a securement platform that is constructed of a soft, pliable or flexible material, such as a soft polymer. In some instances, the securement platform comprises a soft, polymer material comprising a Shore A durometer hardness of from approximately 15 to 100. In some instances, the soft, polymer material comprises a durometer hardness of from approximately 30 Shore A to approximately 90 Shore D. In some instances, the soft, polymer material comprises a durometer hardness of from approximately 50 Shore A to approximately 90 Shore D. In some instances, the distal end of the catheter adapter comprises an intravenous catheter in fluid communication with the lumen. Further, the proximal end of the catheter adapter comprises an extension tube that is also in fluid communication with the lumen. In some instances, securement platform may further comprise a hard or rigid plastic polymer material.

Some implementations of the present invention further comprise a needle hub comprising a rigid material, such as a hard plastic material. The needle hub comprises an open end, a closed end, and a compartment interposed therebetween. The closed end is configured to receive a terminal end of the extension tube, and the open end is configured to receive the proximal end of the catheter adapter, wherein the extension tube is stored within the compartment. In some instances, the extension tube is wound around an outer surface of the needle hub. In some instances, the closed end further comprises a flashback chamber in fluid communication with an interior lumen of the introducer needle.

In some instances, the needle hub further comprises a paddle grip positioned in proximity to the open end and arranged to overlap the securement platform, thereby permitting the user to pinch the paddle grip and securement platform between their thumb and index finger during the process of catheterization. In some instances, the overlapping arrangement of the paddle grip and the securement platform permits the user to hood the tip end of the needle by adjusting their grip to move the securement platform and paddle grip in opposite directions.

The needle hub further comprises an introducer needle having a base end, a tip end, and a body extending therebetween. The base end of the needle is securely attached to the closed end of the needle hub. When assembled, the body of the needle extends outwardly from the closed end, through the proximal end, the lumen, the distal end, and the intravenous catheter, such that the tip end of the needle is exposed beyond a terminal end of the intravenous catheter.

Some implementations of the present invention are further configured such that the body of the introducer needle passes through an interior of the extension tube when the intravenous catheter device is assembled. In some instances, the extension tube is wound around the body of the introducer needle within the compartment.

In some instances, the proximal end of the catheter adapter, and/or the terminal end of the extension tube further comprises a blood control device, such as a valve, a self-sealing polymer, a luer adapter, or a septum. In some instances, the blood control valve comprises a passageway through which the body of the introducer needle passes. In some instances, the blood control device is a single-use device. In other instances, the blood control device is a multi-use device.

Some implementations of the present invention further comprise an extension tube having an access port that is coupled to a sidewall surface of the extension tube, and extending outwardly therefrom. For these embodiments, the needle hub further comprises an access slot extending proximally from the open end to a position that is in proximity to the closed end, whereby the access port passes through the access slot and is located externally to the compartment of the needle hub with the intravenous catheter device is assembled. In some instances, the open end of the needle hub further comprises a notch having a width and depth that is configured to receive and support a proximal edge of the securement platform of the catheter adapter.

Some implementations of the present invention further comprise one or more features designed to capture and shield the tip end of the introducer needle following catheterization of the patient. For example, in some instances the proximal end of the extension tube further comprises a needle shield or safety mechanism that is selectively coupled thereto and through which the body of the introducer needle passes when the device is assembled. Upon removal of the introducer needle from the extension tube, a needle feature, such as a ferrule or notch, actuates the safety mechanism to selectively disengage the safety mechanism from the terminal end of the extension tube. Once released, the safety mechanism captures the tip end of the needle, thereby preventing unintended exposure to the tip end of the needle.

Figure 1B:
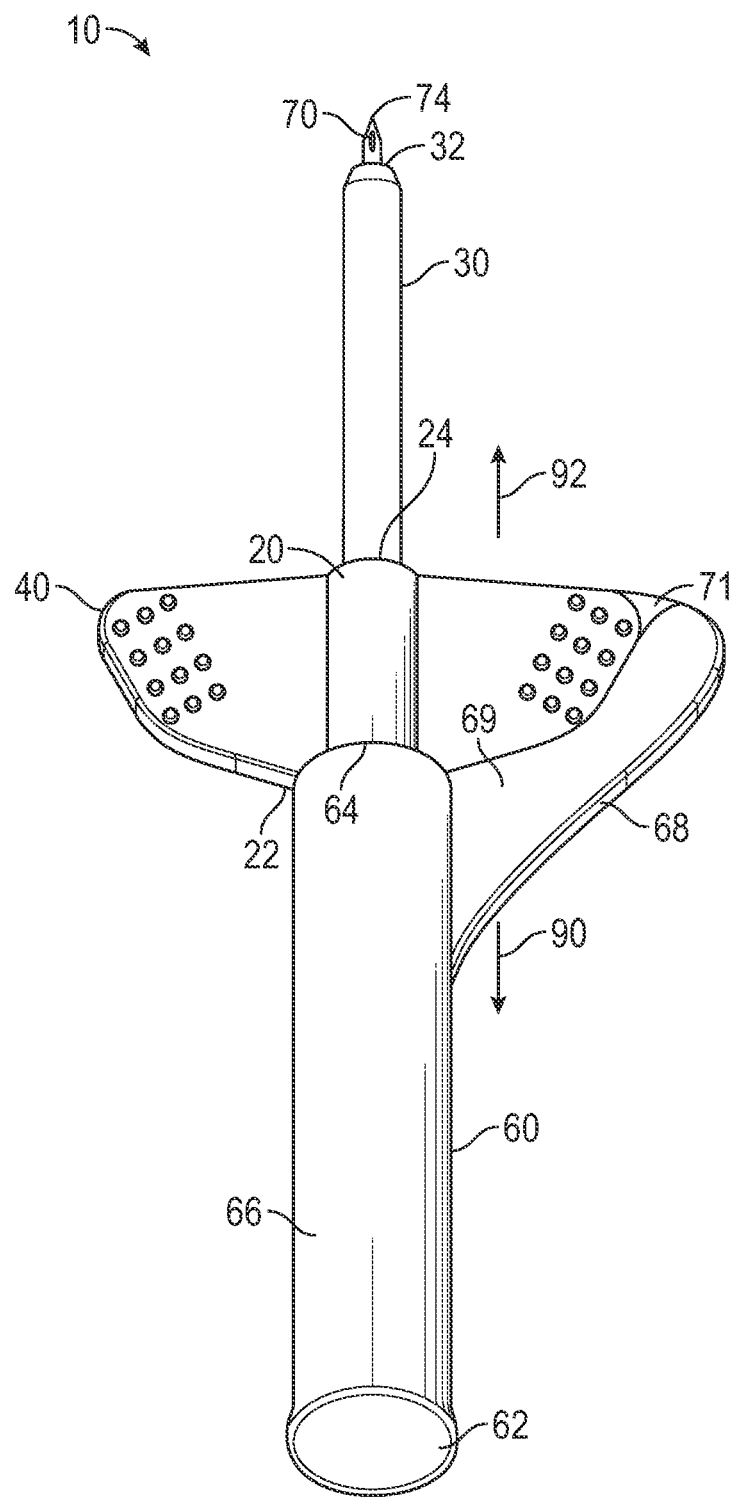
FIG. 1B illustrates a perspective top view of an intravenous catheter device that includes an example nested securement platform in accordance with a representative of the present invention.
Figure 1C:
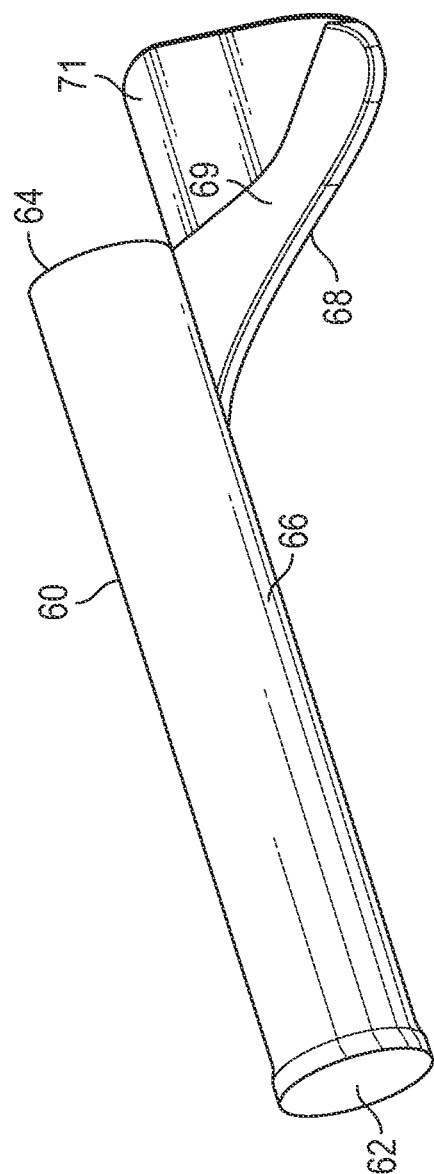
FIG. 1C is an upper perspective view of an example paddle grip of the intravenous catheter device of FIG. 1B in accordance with a representative embodiment of the present invention.
Figure 2:
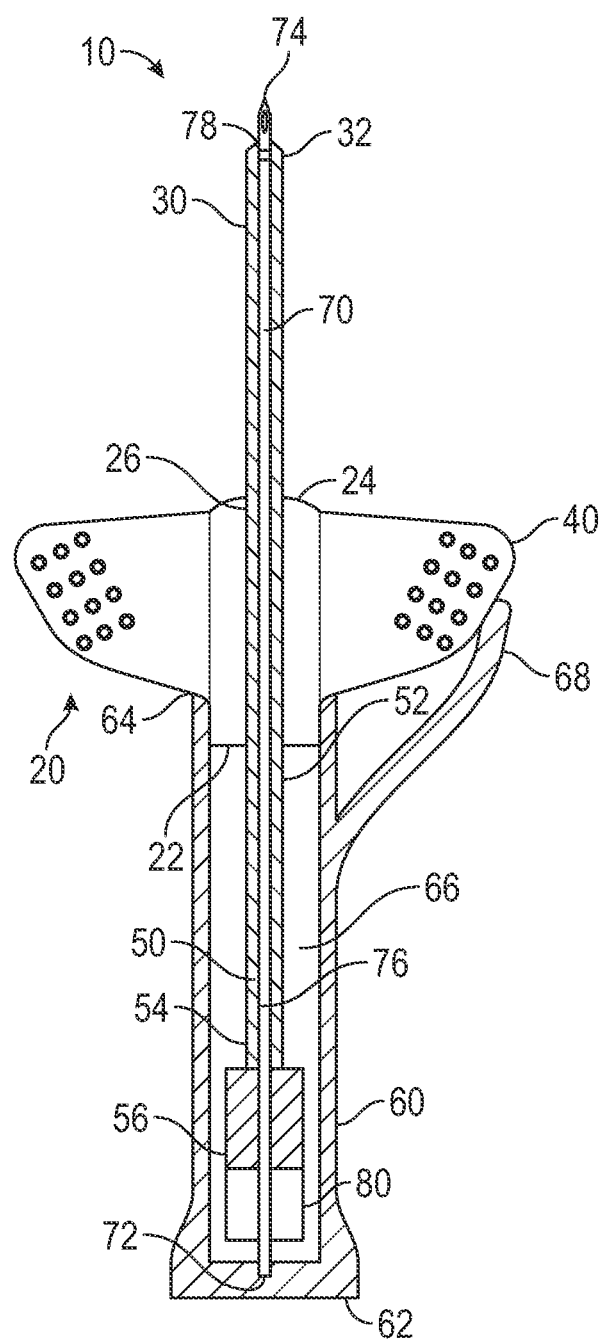
FIG. 2 is a cross-sectioned top view of an assembled intravenous catheter device in accordance with a representative embodiment of the present invention.

With reference to FIGS. 1 and 2, perspective top and cross-sectioned views of an assembled intravenous catheter device 10 are illustrated. In some embodiments, catheter device 10 comprises a catheter adapter 20 having a proximal end 22, a distal end 24, and a lumen 26 extending therebetween. Distal end 24 further comprises an intravenous catheter 30 having a gauge configured to access the peripheral vascular system.

Catheter adapter 20 further comprises one or more securement platforms 40. In some embodiments, securement platforms 40 comprise a soft, pliable polymer material that may easily conform to the contours of the patient's body in proximity to the catheter insertion site, thus providing a low profile securement platform. In some instances, securement platforms 40 comprise a soft polymer material having a Shore A durometer hardness of from approximately 15 to 100, from approximately 20 to 80, from approximately 30 to 70, from approximately 40 to 60, from approximately 45 to 55, or approximately 50. In some instances, a soft, polymer material comprises a Shore A durometer hardness of less than 15. In some instances, a soft, polymer material comprises a Shore A durometer hardness of greater than 100. In some instances, both catheter adapter 20 and securement platform 40 comprise a soft, pliable polymer material.

Proximal end 22 of catheter adapter 20 further comprises an extension tube 50 having a first end 52 coupled to proximal end 22, and further comprises a distal end 54 having a blood control device 56. In some instances, extension tube 50 and catheter 30 comprise a single, monolithic structure or component. In other instances, extension tube 50 and catheter 30 are separate devices or components that are each independently coupled to lumen 26, such that extension tube 50, catheter 30, and lumen 26 are in fluid communication. In some instances, lumen 26 further comprises a blood control device, such as a one-way valve or septum (not shown).

In some embodiments, the septum may have a "low friction" or "low drag" design configured to provide relatively low resistance to withdrawal of an introducer needle 70 proximally through the septum, which occurs as the catheter device 10 transitions from an insertion configuration to a fluid delivery configuration. The resistance to withdrawal of the needle 70 through the septum may be sufficiently low that the clinician can relatively easily move the catheter device 10 from the insertion configuration to the fluid delivery configuration with only a single hand. In some embodiments, the resistance to withdrawal may be, on average, less than about 50 gf.

In some instances, a proximal end of catheter adapter 20 is extended proximally (not shown) to provide extension tube 50. Thus, the proximal end of catheter 30 terminates within the lumen 26 of catheter adapter 20, and extension tube 50 extends outwardly from catheter adapter 20, wherein catheter 30, lumen 26, and extension tube 50 are in fluid communication. In some instances, a portion of securement platform 40 is extended (not shown) to provide extension tube 50.

In some embodiments, blood control device 56 comprises a luer adapter configured to compatibly receive a luer connector coupled to a length of intravenous tubing, or provide access via a needle or syringe. In some instances blood control device 56 further comprises a valve, the septum, and/or a self-healing polymer that permits selective access to the interior lumen of extension tube 50. In some instances, blood control device 56 comprises a single-use valve. In other instances, blood control device 56 comprises a multi-use valve. Blood control device 56 may further comprise a septum actuator configured for use with a single-use or multi-use valve. When not accessed, blood control device 56 retains fluids within catheter 30, catheter adapter 20, and extension tube 50.

Catheter device 10 further comprises a needle hub 60. Needle hub 60 comprises a closed end 62, an open end 64, and a compartment 66 interposed therebetween. Closed end 62 is the proximal-most end of catheter device 10 and is configured to receive a terminal end 54 of extension tube 50. Open end 64 is located opposite of closed end 62 and is configured to compatibly receive proximal end 22 of catheter adapter 20. In some instances, compartment 66 comprises a length sufficient to receive the entire length of extension tube 50. For example, in one embodiment compartment 66 comprises a length from approximately 0.5 inches to approximately 8 inches, from approximately 1 inch to approximately 7.5 inches, from approximately 2 inches to approximately 7 inches, from approximately 3 inches to approximately 6 inches, from approximately 4 inches to approximately 5 inches, or approximately 4.5 inches. In one embodiment, compartment 66 is approximately 4 inches.

Catheter device 10 further comprises the introducer needle 70. Introducer needle 70 comprises a hollow metal or rigid plastic cannula having a base end 72 that is securely attached to closed end 62 within compartment 66. Needle 70 further comprises a sharpened tip end 74 that is opposite base end 72. The body 76 of needle 70 has a length that is greater than the combined lengths of catheter adapter 20, catheter 30, and needle hub 60, when assembled, such that tip end 74 is exposed distally beyond a terminal end 32 of catheter 30. As such, tip end 74 is exposed and capable of providing access through the patient's skin to introduce catheter 30 into the patient's vein.

In some embodiments, introducer needle 70 is threaded through extension tube 50, lumen 26, and catheter 30 prior to catheterization. In this way, introducer needle 70 aligns and coordinates the relative positions of each of the various components.

Various embodiments of the present invention further comprise a safety mechanism 80 configured to secure the sharpened, distal tip 74 of the introducer needle 70 following removal and separation of the needle hub 60 from the catheter adapter 20. A safety mechanism may include any compatible device known in the art. In some instances, the safety mechanism is configured to interact with a needle feature, such as a ferrule, notch, crimp or bump on the cannula. The crimp or bump formed in the cannula cause a slight out of round configuration that can be used to activate a safety mechanism. In some instance, the safety mechanism comprises an arm or lever that is actuated to capture the needle tip within the mechanism and prevent the tip from emerging prior to safe disposal.

The safety mechanism is attached to the body of the needle and is capable of sliding along the length thereof. In some instances, an initial or assembled position of the safety mechanism is located in proximity to the base or proximal end of the needle adapter prior to catheterization. For some configurations, the assembled position of the safety mechanism is between the proximal end of the needle hub and the proximal end of the catheter adapter or securement platform, wherein the safety mechanism does not overlap the catheter adapter or securement platform. In some instances, a portion of the safety mechanism is positioned within the catheter adapter, with the balance of the safety mechanism being positioned external to the catheter adapter, such as within the needle hub. In some embodiments, a portion of the catheter adapter or securement platform is extended proximally to provide a housing in which at least a portion of the safety mechanism is house. In some instance, the entire safety mechanism is housed within the housing of the catheter adapter or securement platform prior to catheterization.

In some embodiments, the assembled position of the safety mechanism positions the proximal end of the catheter adapter between the distal end of the safety mechanism and a distal end of a paddle grip of the needle hub. In some instances, the assembled position of the safety mechanism positions the proximal end of the catheter adapter between the distal end of the safety mechanism and a proximal end of a paddle grip of the needle hub. In some instances, a portion of the safety mechanism overlaps a portion of a paddle grip of the needle hub. In some embodiments, at least some portion of at least one of the catheter adapter and the paddle grip overlaps at least some portion of the safety mechanism. In some embodiments, no portion of the catheter adapter or paddle grip overlaps any portion of the safety mechanism.

In some embodiments, a defeatable mechanical connection is provided between the safety mechanism and at least one other component of the intravenous catheter device. In some embodiments, a distal end of the safety mechanism is selectively coupled to a proximal end of the catheter adapter. In one embodiment, the safety mechanism interlocks internally to the proximal end of the catheter adapter. In one embodiment, the safety mechanism interlocks externally to the proximal end of the catheter adapter. In some embodiments, a distal end of the safety mechanism is selectively coupled to a proximal end of the securement platform. In some embodiments, a surface of the safety mechanism is selectively coupled to at least one surface of at least one of the catheter adapter, a blood control valve, an extension tube, and the securement platform. In some instances, the mechanical connection is defeated upon securement of the needle tip within the safety mechanism.

In some embodiments, catheter device 10 comprises a safety mechanism 80 through with body 76 of needle 70 is threaded, and which is interposedly positioned between terminal end 54 and closed end 62. Following catheterization and withdrawal of needle 70 from extension tube 50, a needle feature 78 interacts with safety mechanism 80 to trap tip end 74 therein, thereby preventing accidental exposure to tip end 74. Any combination of known needle feature and safety mechanism may be used within the scope of the present invention.

Needle hub 60 further comprises a paddle grip 68 positioned in proximity to open end 64 and arranged to overlap a portion of securement platform 40 when catheter device 10 is assembled. In some embodiments, paddle grip 68 comprises a rigid plastic material. The overlapped arrangement of securement platform 40 and paddle grip 68 permits a user to hold catheter device 10 by pinching the overlapped features or components. In one embodiment, a user pinches the overlapping paddle grip 68 and securement platform 40 in order to insert the catheter into a patient. Once tip end 74 and terminal end 32 are inserted within the patient's vein, the user may hood tip end 74 by adjusting their grip to move paddle grip 68 in a proximal direction 90 while either maintaining the position of securement platform 40, or by simultaneously moving securement platform 40 in a distal direction 92.

Once tip end 74 is hooded, the user may further advance catheter 30 into the patient's vein to a final insertion depth. In some instances, catheter 30 comprises a clear or translucent material through which the user can see, and which provides primary blood flashback to indicate proper insertion of catheter 30. In some instances, catheter adapter 20 and/or needle hub 60 further comprise a clear or translucent material for purposes of blood flashback observation. In some embodiments, needle feature 78 comprises a notch which permits blood within the hollow interior of needle 70 to flow between the outer surface of needle 70 and the interior of catheter 30.

In some embodiments, base end 72 of needle 70 is coupled to a secondary flashback chamber (not shown) that is in fluid communication with tip end 74 and the hollow interior of needle 70. For example, closed end 62 may further be modified to include a secondary flashback chamber. As such, blood may flow through the hollow interior of needle 70 and further flow into the secondary flashback chamber to further indicate proper insertion of catheter 30 prior to separating needle hub 60 and needle 70 from catheter adapter 20, catheter 30, and extension tube 50.

As illustrated in FIGS. 1B and 1C, in some embodiments, the securement platform 40 may be nested in the paddle grip 68 in the assembled position or insertion configuration. In further detail, in some embodiments, the paddle grip 68 may include a peripheral ridge 69 disposed along an outer edge of the paddle grip 68. In some embodiments, the peripheral ridge 69 may define a boundary of a distal recess 71 of the paddle grip 40. In some embodiments, the securement platform 40 may be disposed within the distal recess 71 in the insertion configuration. In some embodiments, a curvature of an outer edge of the securement platform 40 may correspond to a curvature of an inner edge of the peripheral ridge 69 such that the securement platform 40 fits within the distal recess 71 in the insertion configuration.

In some embodiments, the peripheral ridge 69 may act as a pull feature. In some embodiments, the peripheral ridge 69 may be positioned such that a digit can easily contact an apex and/or a distal side of the peripheral ridge 69 to apply proximal pressure on the paddle grip 68. In some embodiments, the peripheral ridge 69 may be disposed outward of an outer edge of the securement platform 40 when the intravenous catheter device 10 is in the insertion configuration such that the peripheral ridge 69 may be contacted by the digit even when the securement platform 40 is positioned to overlie the paddle grip 68.

Figure 3:
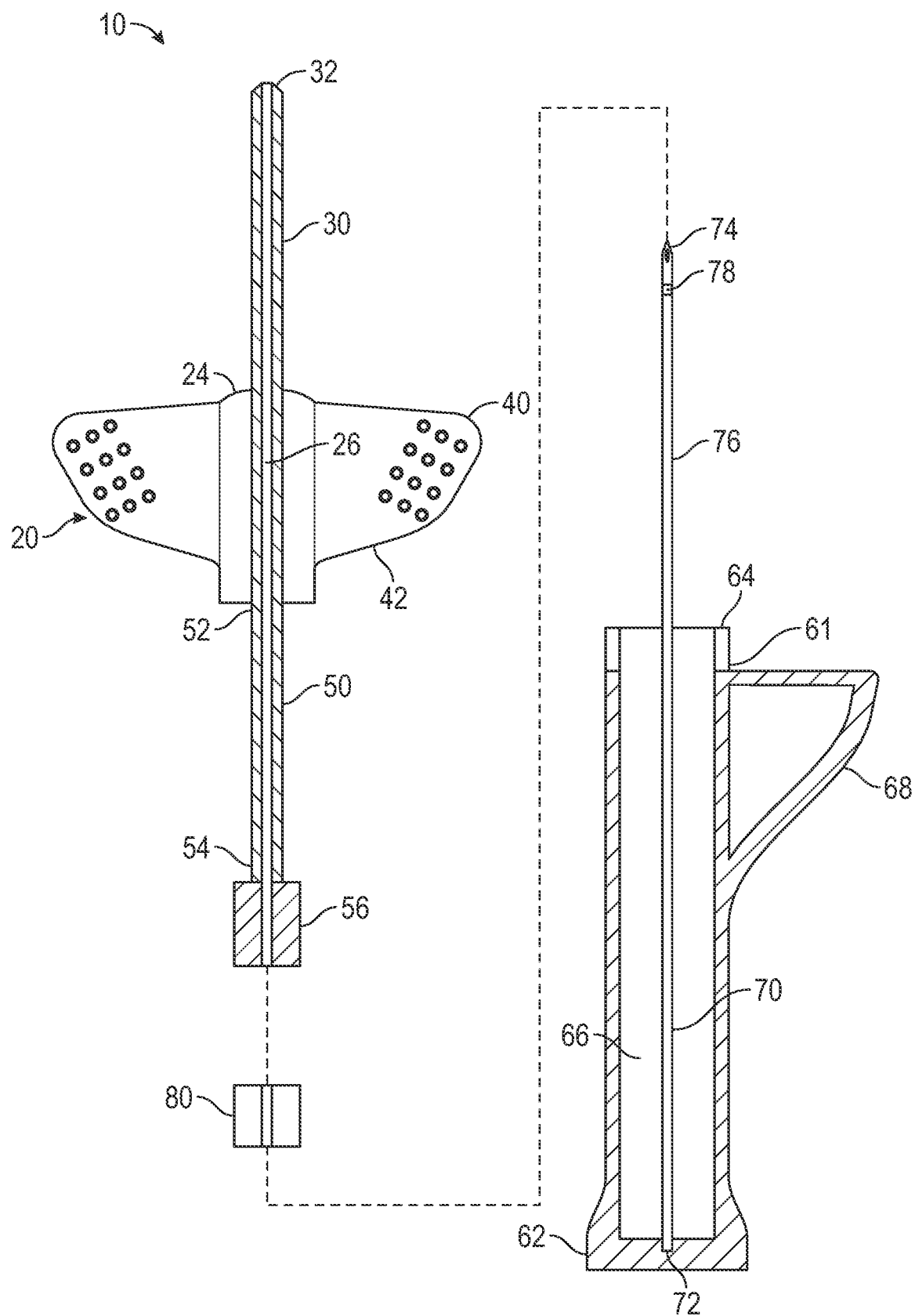
FIG. 3 is an exploded, cross-section top view of an intravenous catheter device in accordance with a representative embodiment of the present invention.

Referring now to FIG. 3, an exploded, cross-sectioned view of catheter device 10 is shown. In some embodiments, open end 64 of needle hub 60 further comprises a notch 61 having a width and depth sufficient to receive and support a proximal edge 42 of securement platform 40. In some instances, notch 61 comprises a depth sufficient to achieve an overlapped arrangement of securement platform 40 and paddle grip 68 when proximal edge 42 is fully inserted within notch 61. In some instances, with width of notch 61 is slightly greater than the thickness of securement platform 40, such that securement platform 40 may easily slide within notch 61, and notch 61 maintains the axial position of catheter adapter 20 within open end 64, and further provides a buttressing support to the soft, pliable material of securement platform 40.

Figure 4A:
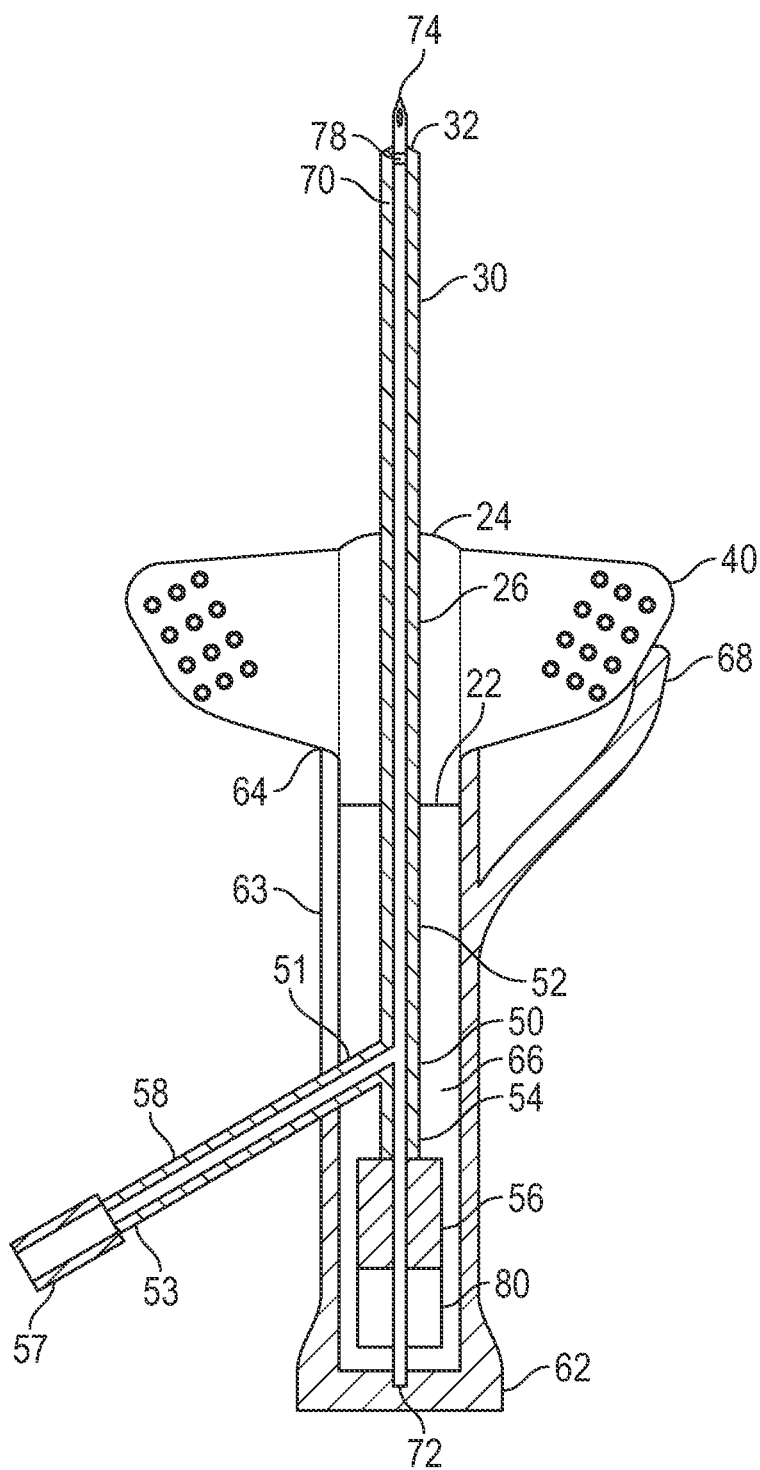
FIG. 4A is a cross-sectioned top view of an assembled intravenous catheter device having an access line in accordance with a representative embodiment of the present invention.
Figure 4B:
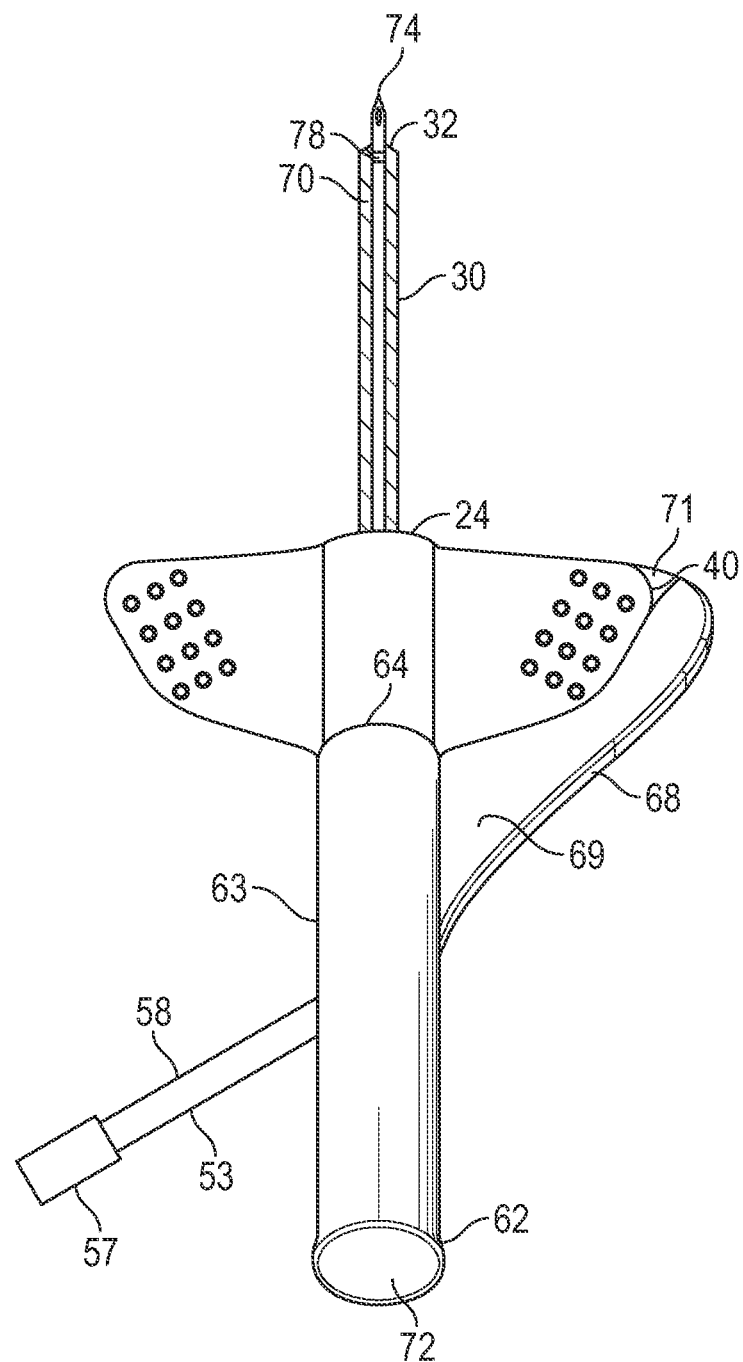
FIG. 4B is a perspective top view of an assembled intravenous catheter device that includes an example nested securement platform in accordance with a representative of the present invention.
Figure 5:
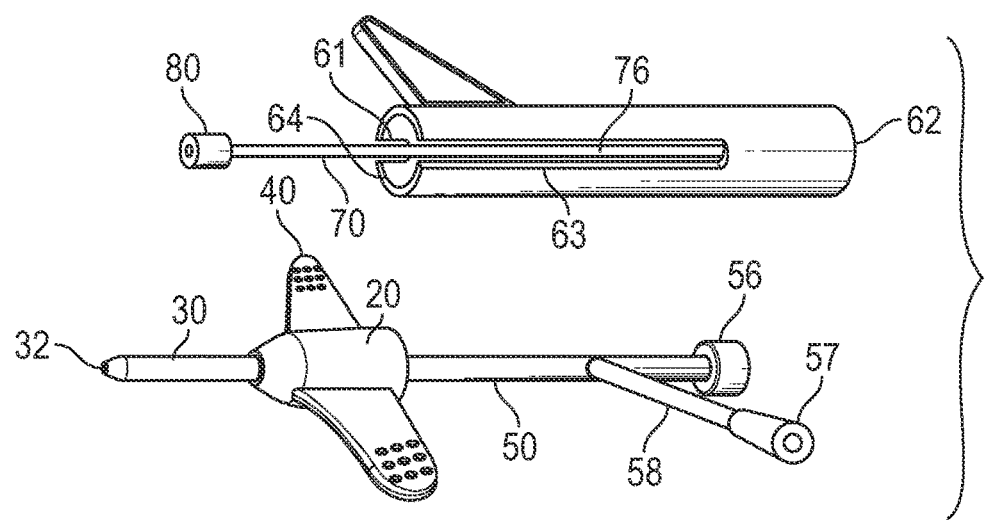
FIG. 5 is a perspective side view of the disassembled intravenous catheter device of FIG. 4A in accordance with a representative embodiment of the present invention.

Referring now to FIGS. 4 and 5, some embodiments of the present invention further comprise an access port 58 comprising a first end 51 coupled to, and in fluid communication with extension tube 50, and further comprising a second end 53 extending outwardly from extension tube 50 and comprising a blood control device 57. Access port 58 may comprise any structure or length within the teachings of the present invention. In some embodiments, access port 58 extends outwardly from the side or sidewall of extension tube 50 at an angle to resemble a y-port. In some instances, access port 58 extends outwardly in a proximal direction. In other instances, access port 58 extends outwardly in a distal direction. In some instances, access port 58 is used to pre-prime extension tube 50 and catheter 30 prior to catheterization.

Blood control device 57 may comprise any structure, shape or feature within the teachings of the present invention, or as is commonly known and practiced in the art. Further, blood control device 57 may be coupled to any secondary intravenous device, including but not limited to, intravenous extension tubing, a syringe, a needle, a cap, a secondary flash chamber, a y-port adapter, a vial, an IV bag, a valve, and a clamp.

Unlike blood control device 56, blood control device 57 is located outside compartment 66, and therefore may include features that may be incapable of being stored within compartment 66. For example, in one embodiment blood control device 57 comprises a y-port. In one embodiment, blood control device 57 comprises one or features in common with blood control device 56, as discussed previously. Access port 58 may further comprise one or more features that may be incompatible for storage within compartment 66. For example, in one embodiment access port 58 comprises a roller clamp, a pinch clamp, or a similar device to control fluid flow therethrough.

In some instances, access port 58 is directly coupled to blood control device 56. In some embodiments, access port 58 extends from catheter adapter 20. In some embodiments, catheter device 10 comprises a first access port coupled to and extending from catheter adapter 20 (not shown), and further comprises a second access port 58 that is coupled to extension tube 50 or blood control device 56.

In some embodiments, needle hub 60 further comprises an access slot 63 extending proximally from open end 64 to closed end 62 to accommodate access port 58. Access slot 63 generally comprises a length selected to correspond to the position of access port 58 when catheter device 10 is assembled. Access port 63 further comprises a width that is slightly larger than the outer diameter of access port 63, whereby access port 63 is able to free slide within access slot 63.

As illustrated in FIG. 4B, in some embodiments, the securement platform 40 may be nested in the paddle grip 68 in the assembled or insertion configuration, similar to the nesting of the securement platform 40 in the paddle grip 68, illustrated in FIG. 1B.

Figure 6A:
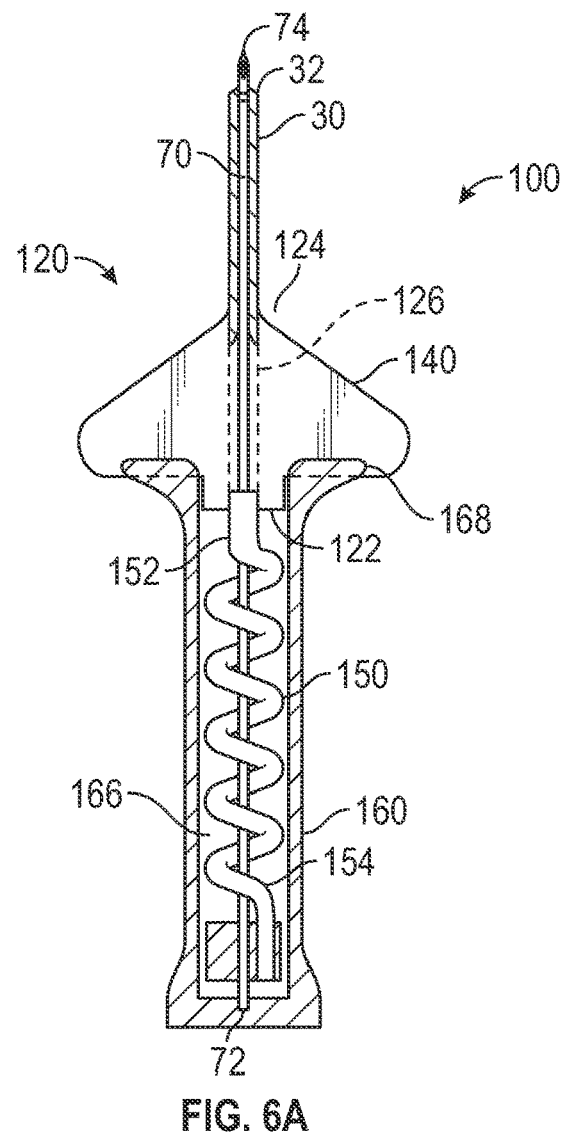
FIG. 6A is cross-sectioned top view of an assembled intravenous catheter device in accordance with a representative embodiment of the present invention.
Figure 6B:
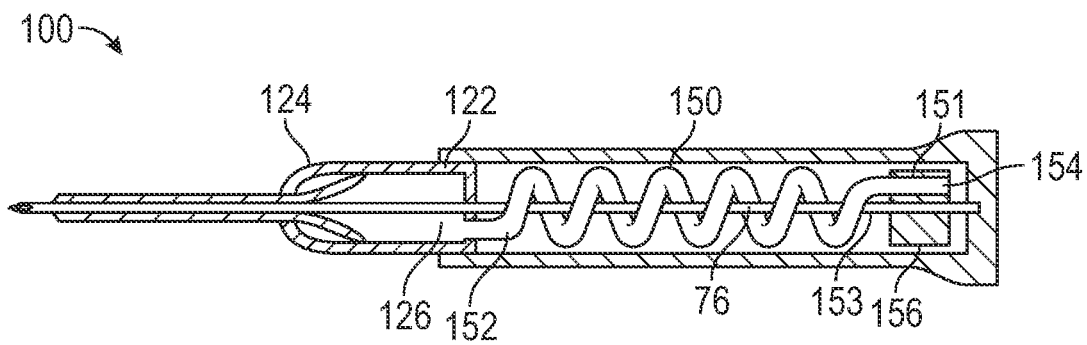
FIG. 6B is a cross-sectioned side view of an assembled intravenous catheter device in accordance with a representative embodiment of the present invention.
Figure 6C:
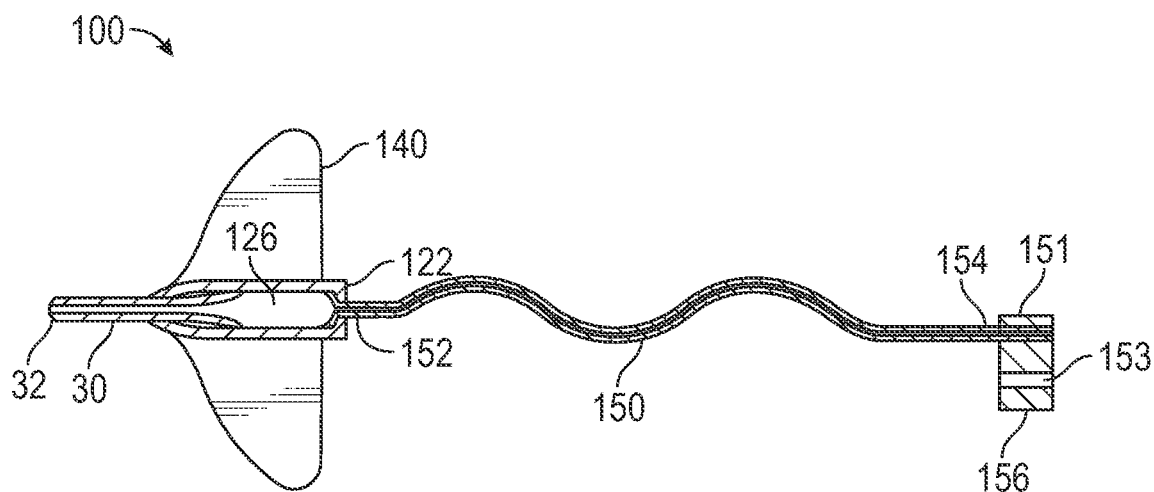
FIG. 6C is a cross-sectioned top view of a catheter adapter and extension tube following removal of the introducer needle and needle hub in accordance with a representative embodiment of the present invention.

Referring now to FIGS. 6A-6C, some embodiments of the present invention further comprise a catheter device 100 having an elongated extension tube 150, wherein the length of extension tube 150 is greater than the length of compartment 166. In some instances, the excess length of extension tube 150 is wrapped around body 76 of needle 70 to accommodate storage within compartment 166 prior to catheterization. Following catheterization, extension tube 150 is unwound from needle 70 as needle 70 and needle hub 160 are separated and removed from catheter adapter 120.

In some embodiments, catheter adapter 120 comprises a lumen 126 having a distal end 124 and a proximal end 122. Distal end 124 comprises intravenous catheter 30, as discussed previously. In some embodiments, proximal end 122 comprises a first surface to which first end 152 of extension tube 150 is coupled and in fluid communication with lumen 126. First end 152 is coupled to proximal end 122 at an off-center position, such as in proximity to the perimeter edge of proximal end 122.

Proximal end 122 further comprises a second surface through which needle 70 passes. In some instances, the second surface of proximal end 122 is the axial center of proximal end 122. In some embodiments, second surface of proximal end 122 comprises a blood control device, such as septum or self-healing polymer through which needle 70 is passed. Upon removal of needle 70 from proximal end 122, the blood control device prevents fluid from passing through the second surface of proximal end 122, thereby directing fluid flow through extension tube 150 at the first surface of proximal end 122.

Similarly, blood control device 156 comprises a first aperture 151 to which is secured the distal end 154 of extension tube 150. In some instances, first aperture 151 is located at an off-center position, such as in proximity to the perimeter edge of blood control device 156. Blood control device 156 further comprises a second aperture 153 through which needle 70 passes. In some instances, second aperture 153 is located at the axial center of blood control device 156. Upon catheterization, blood control device 156 retains fluid within extension tube 150 until further accessed by a secondary intravenous device, such as a luer connector, a syringe, a needle, or other device.

In some embodiments, needle hub 160 comprises a pair of truncated paddle grips 168 having slots that receive the proximal edges of securement platforms 140. In some instances, the dimensions and shape of paddle grips 168 and securement platforms 140 are configured to accommodate catheterization by pinching these elements between the user's thumb and index finger. In some embodiments, each of the securement platforms 140 may be nested in one of the paddle grips 168 in the assembled position or insertion configuration, similar to the nesting of the securement platform 40 in the paddle grip 68, illustrated in FIGS. 1B and 4B.

Figure 7:
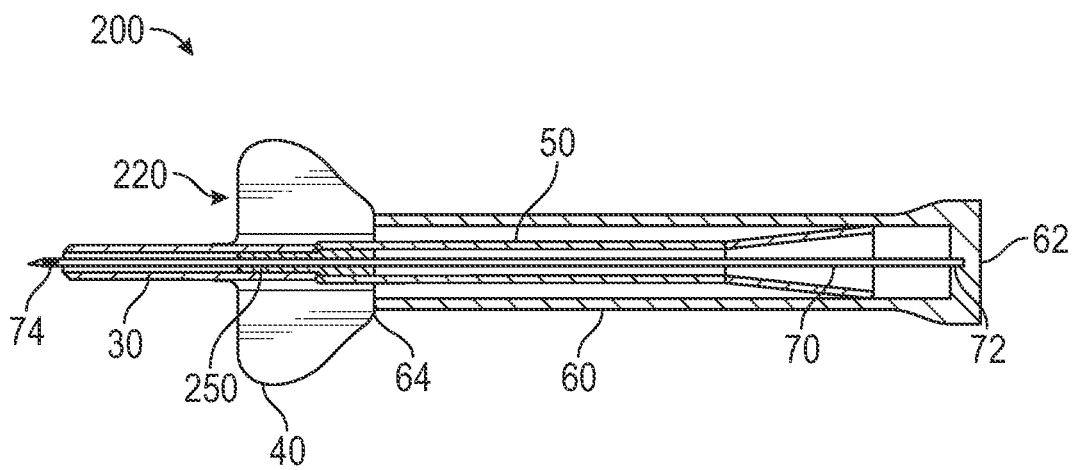
FIG. 7 is a cross-sectioned top view of an intravenous catheter device having second cannula fixedly secured within the catheter and configured to receive the outer diameter of the introducer needle in accordance with a representative embodiment of the present invention.

In some instances, the small gauge and extended length of introducer needle 70 may result in undesirable flexing or bending of needle 70 during catheterization. Accordingly, in some embodiments catheter device 200 comprises a sleeved needle configuration, as shown in FIG. 7. In some instances, catheter 30 comprises a second cannula 250 having an inner diameter that is configured to receive the outer diameter of needle 70. Second cannula 250 may comprise a truncated length and be securely fixed within the interior lumen or fluid pathway of catheter 30. In some instances, second cannula 250 is fixed within the portion of catheter 30 that is located within catheter adapter 220. Second cannula 250 therefore acts as a sheath for the portion of needle 70 located within catheter adapter 220. In some instances, second cannula 250 supports and stiffens needle 70 against undesired flexing or bending.

In some instances, catheter device 200 comprises a tapered introducer needle (not shown), wherein the base and middle portions of the tapered needle comprises a gauge and thickness that is greater than the gauge of the distal end and tip portion of the needle. The tapered configuration imparts greater stiffness to the proximal and middle portions of the needle, which serve to stiffen the distal and tip portions of the needle, thereby reducing undesired flexing or bending of the needle during catheterization. Further still, in some embodiments catheter device 200 comprises an introducer needle having base and middle portions comprising a first gauge, and distal and tip portions comprising a second gauge, wherein the first gauge is greater than the second gauge, and the first gauge imparts stiffness to the second gauge.

In some embodiments, a particular catheter device, such as, for example, the catheter device of any of the FIGS. 1-7, may include a needle safety mechanism. The safety mechanism may include any safety mechanism configured to secure a sharpened, distal tip of an introducer needle when the needle is withdrawn from a catheter of the particular catheter device, preventing accidental needle sticks.

The safety mechanism may be coupled with the particular catheter device in any number of ways. In some embodiments, the safety mechanism may include an internal interlock in which the safety mechanism is coupled with an internal surface of a catheter adapter. Coupling may include threading, fitting, snapping, connecting, attaching, fastening, clipping, hooking, or any other suitable means of coupling. Non-limiting examples of safety mechanisms that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; U.S. Patent Application No. 62/314,262, titled CANNULA CAPTURE MECHANISM, filed Mar. 28, 2016, each of which is herein incorporated by reference in its entirety. In some embodiments, the safety mechanism may include a clip disposed within the catheter adapter, a non-limiting example of which is provided in U.S. Pat. No. 6,117,108, titled SPRING CLIP SAFETY IV CATHETER, filed Jun. 12, 1998, which is herein incorporated by reference in its entirety.

In some embodiments, the safety mechanism may include an external interlock in which the safety mechanism is coupled with an external surface of the catheter adapter. In some embodiments, the safety mechanism may be coupled with an external surface of the catheter adapter and an internal and/or external surface of a needle hub. Coupling may include threading, fitting, snapping, connecting, attaching, fastening, clipping, hooking, or any other suitable means of coupling. Non-limiting examples of safety mechanisms that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the safety mechanism may include a V-clip or a similar clip. A non-limiting example of a V-clip is provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. The V-clip may selectively retain a portion of the catheter adapter.

In some embodiments, a defeatable mechanical connection is provided between the safety mechanism and at least one other component of the IV catheter system. In some instances, the mechanical connection is defeated upon securement of the distal tip of the needle within the safety mechanism. In some embodiments, a surface of the safety mechanism is selectively coupled to one or more of the following: the catheter adapter, a blood control valve, an extension tube, and one or more paddle grips.

In some embodiments, the safety mechanism may include a safety barrel, which may be spring-loaded. For example, the safety barrel may be spring loaded as in the BD™ Insyte® Autoguard™ BC shielded protective IV catheter. In some embodiments, the safety mechanism may be passively and/or actively activated. In some embodiments, the safety mechanism may be configured to interact with a needle feature, such as a ferrule, notch, crimp or bump on the needle. In some embodiments, the safety mechanism may include an arm or lever that may be actuated to capture the distal tip within the safety mechanism and prevent the tip from emerging prior to safe disposal. In some embodiments, the safety mechanism may be attached to a body of the needle and may be capable of sliding along the length thereof.

In some embodiments, in an assembled position prior to catheterization, the safety mechanism may be disposed between the catheter adapter and the needle hub. In some embodiments, the catheter adapter and the needle hub may be spaced apart by at least a portion of the safety mechanism in the assembled position prior to catheterization. In some embodiments, in the assembled position prior to catheterization, a proximal end of the catheter adapter may be disposed between a distal end of the safety mechanism and a distal end of a grip of the needle hub, such as, for example, a paddle grip. In some embodiments, in the assembled position prior to catheterization, the proximal end of the catheter adapter body may be disposed between the distal end of the safety mechanism and a proximal end of the grip of the needle hub. In some embodiments, a portion of the safety mechanism may overlap with a portion of the grip of the needle hub. In some embodiments, at least a portion of at least one of the catheter adapter and the grip overlaps at least some portion of the safety mechanism. In some embodiments, no portion of the catheter adapter body or the grip overlaps any portion of the safety mechanism.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An assembled intravenous catheter device, comprising:
a catheter adapter having a proximal end, a distal end, and a lumen interposed therebetween, the catheter adapter further comprising a securement platform, the distal end of the catheter adapter comprising an intravenous catheter and the proximal end of the catheter adapter comprising an extension tube, the intravenous catheter and the extension tube being in fluid communication with the lumen;
a needle hub having a closed end, an open end, and a compartment interposed therebetween, the closed end being configured to receive a terminal end of the extension tube and the open end configured to receive the proximal end of the catheter adapter, wherein the extension tube is wound around a body of an introducer needle within the compartment; and
the introducer needle having a base end, a tip end, and the body extending therebetween, the base end being securely attached to the closed end of the needle hub, and the body extending through the proximal end of the catheter adapter, the lumen, the distal end of the catheter adapter, and the intravenous catheter such that the tip end of the introducer needle is exposed beyond a terminal end of the intravenous catheter.

2. The assembled intravenous catheter device of claim 1, wherein the proximal end of the catheter adapter further comprises a blood control valve, wherein the body of the introducer needle extends through the blood control valve.

3. The assembled intravenous catheter device of claim 2, wherein the blood control valve comprises a septum.

4. The assembled intravenous catheter device of claim 2, wherein the blood control valve comprises a self-sealing polymer.

5. The assembled intravenous catheter device of claim 1, further comprising a safety mechanism slidably coupled to the body of the introducer needle and configured to capture and retain the tip end of the introducer needle upon removal of the catheter adapter and the extension tube from the needle hub.

6. The assembled intravenous catheter device of claim 1, wherein a proximal end of the extension tube further comprises a blood control valve.

7. The assembled intravenous catheter device of claim 6, wherein the blood control valve further comprises a passageway, wherein the body of the introducer needle extends through the passageway.

8. The assembled intravenous catheter device of claim 6, wherein the blood control valve is a septum.

9. The assembled intravenous catheter device of claim 6, wherein the blood control valve is a self-sealing polymer.

10. The assembled intravenous catheter device of claim 6, wherein the blood control valve is a luer adapter.

11. The assembled intravenous catheter device of claim 1, wherein a gauge of the extension tube is greater than a gauge of the intravenous catheter.

12. The assembled intravenous catheter device of claim 1, wherein the securement platform comprises a pliable, flexible polymer material.

13. The assembled intravenous catheter device of claim 1, wherein the closed end of the needle hub further comprises a flashback chamber.

14. The assembled intravenous catheter device of claim 1, wherein a length of the extension tube is greater than a length of the compartment.

* * * * *